July 5, 1966 J. J. WICKS Plant Pat. 2,656
TOMATO PLANT
Filed Oct. 14, 1964
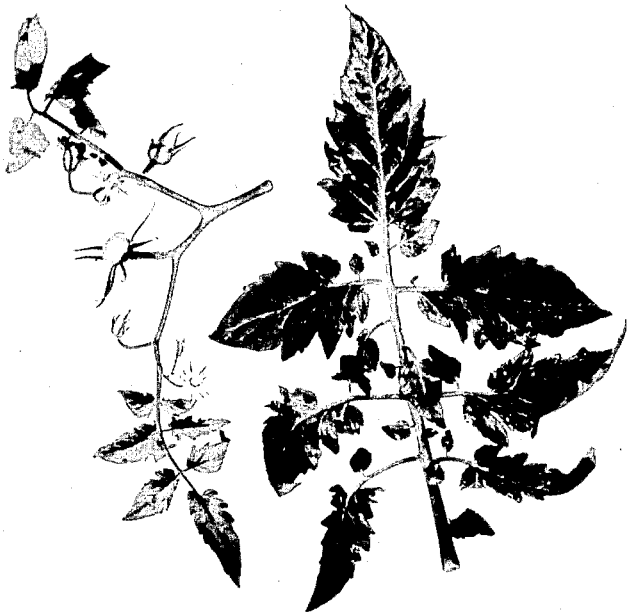
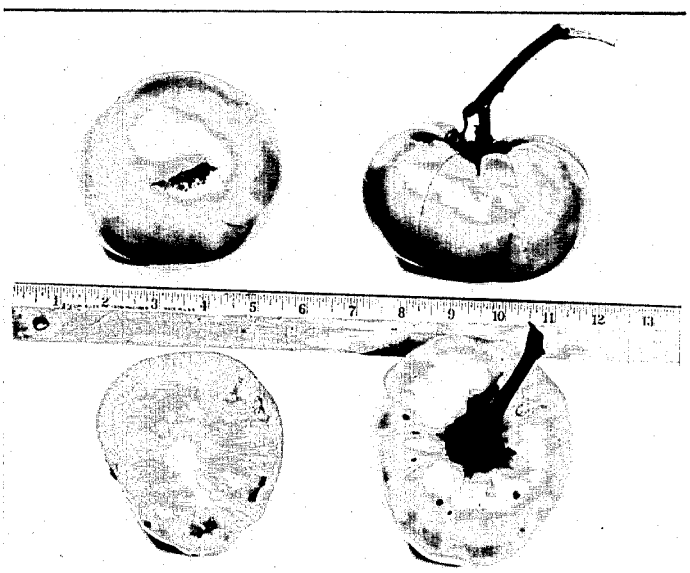
Inventor.
Jacob Jude Wicks
By: Robb & Robb
Attorneys.

United States Patent Office

Plant Pat. 2,656
Patented July 5, 1966

2,656
TOMATO PLANT

Jacob Jude Wicks, New York, N.Y.
(126—12 95th Ave., Richmond Hill, N.Y.)

Filed Oct. 14, 1964, Ser. No. 403,965
1 Claim. (Cl. Plt.—89)

The present invention relates to a new and distinct variety of tomato plant which was originated by me by crossing, through hand-pollination, the variety commercially known as "Manalucie" (unpatented) with the variety commercially known as "New Belgian Giant" (unpatented), the former being the seed parent and the latter being the pollen parent.

As the result of this breeding, I have produced a new and improved variety of tomato plant which is distinguished from its parents, as well as from all other tomato varieties of which I am aware, as evidenced by the following unique combination of characteristics which are outstanding therein:

(1) A strong, bushy and spreading habit of growth resulting in heavy and much-branched vines;

(2) Abundant, somewhat leathery and broad leaves which are deeply split from the margins to almost the midrib, said leaves being a somewhat darker green color than the leaves of either parent;

(3) Thicker, longer and stronger main stems than either parent;

(4) Greater ease of pollination of blossoms, with consequent good fruit production;

(5) Good resistance to Verticillium and Fusarium fungus diseases;

(6) Better resistance to drought than either parent, and good resistance to extremes of sunlight and heat;

(7) A medium to heavy fruit bearing habit;

(8) Prolonged fruit production, averaging about ninety days, beginning between the latter part of May and the middle part of July, depending on seasonal conditions;

(9) Production of exceptionally large and heavy fruit;

(10) A thick-meated fruit texture and relatively sweeter fruit flavor than either parent; and

(11) An attractive Vermilion fruit color.

In comparison with its seed parent "Manalucie," the fruit of the new variety averages about twice as long and one and one-half as wide as the fruit of this parent, while the fruit has a thinner skin and is sweeter in flavor, with the plants being more spreading and having longer and stronger main stems and somewhat darker green leaves, and the plants also having better resistance to drought and fungus diseases.

As compared with its pollen parent "New Belgian Giant," from which the new variety has inherited its characteristic large leaves and large fruit size, the plants are slightly larger in size, the fruit is about three or four inches longer and about two inches wider, when fully grown, than the fruit of this parent, the plants are more spreading and are more abundantly clothed with leaves, the blossoms are more easily pollinated, with consequent greater fruit production, the fruit skin is thicker, and the new variety exhibits better resistance to drought and fungus diseases.

Asexual reproduction of my new variety by budding (shield budding), as performed at Richmond Hill, New York, shows that the foregoing characteristics are fixed and established and come true through succeeding propagations.

The accompanying drawing shows typical specimens of the fruit and vegetative growth of my new variety in different stages of development, with one of the fruit specimens being illustrated in cross-section, all as depicted in color as nearly true as it is reasonably possible to make the same in an illustration of this character.

The following is a detailed description of my new variety, with color terminology in accordance with Wilson's Horticultural Colour Chart, published in collaboration with The Royal Horticultural Society, as based on observations made from plants and fruit grown at Richmond Hill, New York, and also at Smithtown, Long Island:

Type: Large; spreading; bushy; heavy bearer.

Breeding: Seedling.

*Seed parent.*—"Manalucie."

*Pollen parent.*—"New Belgian Giant."

Propagation: Holds its distinguishing characteristics through succeeding propagations by budding.

Plant:

*Habit.*—Bushy; somewhat spreading, but tall and leafy in early stages; much-branched.

*Growth.*—Average; large; strong vines.

*Foliage.*—Leaves—usually compound of 7 leaflets when mature; abundant; moderately heavy; somewhat leathery. Leaflets: Shape—pointed-oval in general, with margins waved and deeply serrated to almost the midrib for about ⅔ of length from base. Size (mature)—length—from about 8 inches to 10 inches; width—from about 4 inches to 5 inches. Color—near Spinach Green, Plate 0960; somewhat darker than either parent.

*Main stems.*—Thicker, longer and stronger than those of either parent.

*Branches.*—Same as in main stems.

*New Shoots.*—Same as in main stems.

Fruit:

*Borne.*—Heavily; usually from 20 to 25 fruits per plant.

*Shape.*—Somewhat irregular but generally oblong and flattened, with crevasses beginning at stem and extending to margins.

*Size.*—Heavy; average weight of 1 pound. Length—from about 5 inches to 8 inches. Width—from about 4 inches to 6 inches. Height—from about 3 inches to 4 inches.

*Texture.*—Thick-meated.

*Color.*—Near Vermilion, Plate 18, both inside and outside.

*Bearing season.*—About 90 days, beginning between latter part of May and middle part of July, depending on seasonal conditions.

*Flavor.*—Relatively sweeter than fruit of both parents.

*Skin.*—Thinner than "Manalucie," but thicker than "New Belgian Giant."

Disease resistance: Good resistance to Verticillium and Fusarium fungus diseases, as determined by comparison with parent varieties and other varieties which become infected under the same cultural conditions as grown at Richmond Hill, New York, and also at Smithtown, Long Island.

Drought resistance: Good, as determined in the same manner as disease resistance.

I claim:

A new and distinct variety of tomato plant, substantially as herein shown and described, characterized particularly as to novelty by the unique combination of a strong, bushy and spreading habit of growth resulting in heavy and much-branched vines, abundant, somewhat leathery and broad leaves which are deeply split from the margins to almost the midrib, said leaves being a somewhat darker green color than the leaves of either parent, thicker, longer and stronger main stems than either parent, greater ease of pollination of blossoms, with consequent good fruit production, good resistance to Verticillium and Fusarium fungus diseases, better resistance to drought than either parent, and good resistance to extremes of sunlight and heat, a medium to heavy fruit bearing habit, prolonged fruit production, averaging about ninety days, beginning between the latter part of May and the middle part of July, depending on seasonal conditions, production of exceptionally large and heavy fruit, a thick-meated fruit texture and relatively sweeter fruit flavor than either parent, and an attractive Vermilion fruit color.

No references cited.

ABRAHAM G. STONE, *Primary Examiner.*

R. E. BAGWILL, *Assistant Examiner.*